(12) United States Patent
Al-Hamouz et al.

(10) Patent No.: US 8,906,972 B1
(45) Date of Patent: Dec. 9, 2014

(54) AQUEOUS TWO PHASE (ATPSS) OF PH-RESPONSIVE POLY(PHOSPHONATE-ALT-SULFUR DIOXIDE) WITH PEG

(71) Applicants: King Fadh University of Petroleum and Minerals, Dhahran (SA); King Abdulaziz City for Science and Technology, Riyadh (SA)

(72) Inventors: Othman Charles Sadeq Al-Hamouz, Dhahran (SA); Shaikh Asrof Ali, Dhahran (SA)

(73) Assignees: King Fahd University of Petroleum and Minerals, Dhahran (SA); King Abdulaziz City of Science and Technology, Riyadh (SA)

( * ) Notice: Subject to any disclaimer, the term of this patent is extended or adjusted under 35 U.S.C. 154(b) by 0 days.

(21) Appl. No.: 14/142,191

(22) Filed: Dec. 27, 2013

(51) Int. Cl.
  *C08J 11/04* (2006.01)
  *C07K 1/14* (2006.01)
(52) U.S. Cl.
  CPC .................................. *C07K 1/145* (2013.01)
  USPC ............... 521/40; 521/31; 210/652; 210/636; 210/639

(58) Field of Classification Search
  USPC ...................... 521/40, 31; 210/652, 636, 639
  See application file for complete search history.

(56) References Cited

U.S. PATENT DOCUMENTS

| | | | |
|---|---|---|---|
| 7,060,669 B1 | 6/2006 | Penttila et al. | |
| 7,335,492 B2 | 2/2008 | Penttila et al. | |
| 8,268,915 B2 | 9/2012 | Johansson et al. | |
| 2010/0184210 A1 | 7/2010 | Rossmanith et al. | |

OTHER PUBLICATIONS

Ali et al., Separation and Purification Technology 98 (2012) 94-101.*
Othman Charles S. Alhamouz et al., Aqueous Two-Phase Systems of pH-Responsive Poly[sodium(diallylamino)methylphosphonate-*alt*-sulfur dioxide] Cyclopolymer with Poly(oxy thylene), Advanced Search (ACS Publications), pubs.acs.org/action/doSearch?action=search&author=Al%5C-Hamouz%2C+O+C+S&qsSearchArea=author&&, 2 pages, 2013.

* cited by examiner

*Primary Examiner* — Shane Fang
(74) *Attorney, Agent, or Firm* — Oblon, Spivak, McClelland, Maier & Neustadt, L.L.P.

(57) ABSTRACT

An aqueous two-phase system (ATPS) containing a poly (oxyethylene) (POE) and a poly[sodium (diallylamino)alylphosphonate-alt-sulfur dioxide] form a pH-responsive dianionic polyelectrolyte (DAPE). The two polymers form ATPS's at low concentrations, where the addition of HCl changes the charge types and their densities on the polymer chains.

8 Claims, 5 Drawing Sheets

Polyelectrolyte Effect

FIG. 4B

Antipolyelectrolyte Effect

AQUEOUS TWO PHASE (ATPSS) OF PH-RESPONSIVE POLY(PHOSPHONATE-ALT-SULFUR DIOXIDE) WITH PEG

BACKGROUND OF THE INVENTION

Technical Field

The present invention relates to a pH-responsive dianionic polyelectrolyte polymer, a process for synthesizing the pH-responsive dianionic polyelectrolyte polymer, an aqueous two-phase system (ATPS) comprising the pH-responsive dianionic polyelectrolyte polymer, a method for purifying proteins using the ATPS, and a process for recycling the ATPS system.

Description of Related Art

Liquid-liquid extraction in an aqueous two-phase system (ATPS) is a powerful technique for isolation and purification of proteins. The separation of macromolecules and particles by means of liquid-liquid extraction is well known. Mainly polyethylene glycol (PEG)-salt, PEG-dextran and PEG-starch systems have been used. More recently detergents and detergents with reversed solubility were discovered as suitable methods for separation of macromolecules, and especially for the separation of proteins.

An advantage of aqueous two-phase systems (ATPS) is that they are especially suited for large scale processing of microbial proteins not only from culture supernatants but also from crude extracts containing cells and cell debris. Characteristic features of biological fluids as well as suspensions include rather small particle sizes, low density differences between fluid and suspended solids, high viscosities of the extracts and high compressibility of the solids. These attributes decrease the performance of conventional methods for solid-liquid separation like centrifugation and filtration at the beginning of a protein recovery process. Using an aqueous two-phase system removal of solids can be integrated into a liquid-liquid separation step, clarification is thus combined with an initial purification.

After the extraction process phase separation can be accomplished by settling under gravity as well as by centrifugation. ATPS can be applied in various scales from very small laboratory scale to large industrial scale thus suiting for various proteins, purposes and needs. With regard to industrial purposes commercially available centrifugal separators can be used to shorten separation time. The potential of centrifugal separators of various design for processing of large volumes of aqueous two phase systems has been investigated. Polymer/polymer or polymer/salt systems were used to demonstrate the feasibility of continuous separation of aqueous two-phase systems in centrifugal separators.

Extraction systems based on nonionic surfactants have been described as an alternative to standard polymer/polymer or polymer/salt systems. Phase forming surfactants include, e.g., polyoxyethylene type nonionic detergents. The basis of this type of aqueous two-phase system is the temperature dependent reversible hydration of the polar ethylene oxide head groups. The temperature at which the phase separation occurs is referred to as the cloud-point (cloud-point extraction). This kind of aqueous two-phase system is especially suited for the extraction of amphiphilic biomolecules. The potential of this type of two-phase system for separating membrane bound proteins from cytosolic and peripheral membrane proteins has been demonstrated. Lamellar structures formed in the miscibility gaps of polyglycol ether/water systems are responsible for the selective extraction of hydrophobic substances.

In aqueous two phase systems the desired target e.g. a protein should partition selectively into one phase (preferentially the lighter phase) while the other substances should partition into the other phase (preferentially the heavier phase). In PEG/salt and PEG/dextran and similar systems there are several driving forces for a substance like charges, hydrophobic, hydrophilic forces or the dependence on conformation or ligand interaction. The forces leading to separation in detergent based aqueous two phase systems are suggested to be primarily hydrophobic. Conventional ATPS have not provided, a physical picture of the phase behaviour and prediction of such systems is hardly possible.

In ATPS the partitioning coefficient is defined as the concentration (activity in case of an enzyme) of the target in the top phase divided by the concentration (enzyme: activity) of the target protein in the bottom phase. Partitioning coefficients in ATPS systems are usually in the range from less than 1 up to less than 100.

$$K = \frac{C_{i,T}}{C_{i,B}}$$

Yield is defined as the amount of target in the top phase divided by the sum of the amount of target in top and bottom. This leads to the following equation $$Y_T = \frac{1}{1 + \left[\frac{V_B}{V_T} \cdot \frac{1}{K}\right]}$$

If the desired substance is directed to the heavier phase the yield is defined by $$Y_B = \frac{1}{1 + \left[\frac{V_B}{V_T} \cdot K\right]}$$

The volume ratio of the two coexisting phases are defined by the volumes of the lighter over the heavier phase, respectively.

$$R = \frac{V_T}{V_B}$$

Use of ATPS has so far been limited to certain targets. Due to the advantages of ATPS in protein separation, purification and localisation highly selective and powerful methods are needed. This is especially important for large scale processes where ATPS in general is very inexpensive as a first capture step or as the only step for purification, clarification and concentration. The system should be universal so that the technique would be strong enough to mediate separation of in principle any component to the desired phase irrespective of its size or biochemical properties.

Aqueous two-phase systems (ATPSs) comprising two water-soluble polymers in the presence or absence of inorganic salt are of tremendous industrial importance (Albertsson, P. A. "Partition of cell particle and macromolecules," John Wiley: New York, 1986; Johansson, H. O. et al., "Protein partitioning in poly(ethylene glycol)/sodium polyacrylate aqueous two-phase systems." *J. Chromatogr. A.* 2008, 1178, 145-153; Duarte, S. P. et al., "Preparation of plasmid DNA polyplexes from alkaline lysates by a two-step aqueous two-phase extraction process" *J. Chromatogr. A.* 2007, 1164(1), 105-112; Bora, M. M. et al., "Aqueous two-phase partitioning of cephalosporin antibiotics: effect of solute chemical nature," *Sep. Purif. Technol.* 2005, 45, 153-156; Su, C.-K. et al. "Partitioning and purification of lysozyme from chicken egg white using aqueous two-phase system" *Process Biochem.* 2006, 41, 257-263—each incorporated herein by reference in its entirety). The high water content and low interfacial tension in ATPSs provide a benign and compatible environment for efficient purification as well as selective separation of a variety of industrially important labile biomolecules such as proteins (Benavides, J. et al., "Extraction and Purification of Bioproducts and Nanoparticles using Aqueous Two-Phase Systems Strategies," *Chem. Eng. Technol.* 2008, 31, 838-845; Salabat, A. et al., "Amino acids partitioning in aqueous two-phase system of polypropylene glycol and magnesium sulfate," *J. Chromatogr. B: Analyt. Technol. Biomed. Life Sci.* 2007, 858(1-2), 234-238; Andrews, B. A. et al., "Correlation for the partition behavior of proteins in aqueous two-phase systems: effect of surface hydrophobicity and charge," *Biotechnol. Bioeng.* 2005, 90(3), 380-390; Walter, H. D., et al., "Partitioning in Aqueous Two-Phase systems: Theory, Methods, Uses and Application to Bio-technology," Academic Press: Orlando, 1989—each incorporated herein by reference in its entirety). The added advantage of such inexpensive liquid-liquid extraction systems is that they can be readily scaled-up. The separation technique is also becoming increasingly important in non-biotechnology areas such as industrial waste remediation: Notable examples include the utilization of ATPSs in the removal of color from textile plant wastes (Huddleston, J. G. et al., "Separation and recovery of food coloring dyes using aqueous biphasic extraction chromatographic resins biphasic systems," *J. Chromatogr., B: Biomed. Sci. Appl.* 1998, 711, 237-244—incorporated herein by reference in its entirety), and metal ions (Hatti-Kaul, R. "Aqueous Two Phase Systems: Methods and Protocols," Humanae Press: New Jersey, 2000; Vatanpoura, V. et al., "Development of ion imprinted technique for designing nickel ionselective membrane," *J. Membrane Sci.* 2011, 373, 36-42; Shamsipur, M. et al., "Flame photometric determination of cesium ion after its preconcentration with nanoparticles imprinted with the cesium-dibenzo-24-crown-8 complex," *Microchim. Acta.* 2013, 180, 243-252; Rajabi, H. et al., "Development of a highly selective voltammetric sensor for nanomolar detection of mercury ions using glassy carbon electrode modified with a novel ion imprinted polymeric nanobeads and multi-wall carbon nanotubes,"*J. Electroanal. Chem.* 2013, 693, 16-22—each incorporated herein by reference in its entirety) and organic pollutants from the environment (Rogers, R. B. et al., "Partitioning of small organic molecules in aqueous," *J. Chromatogr., B: Biomed. Sci. Appl.* 1998, 711, 255-263—incorporated herein by reference in its entirety). ATPSs based on poly(oxoethylene) (POE) and dextran are the most commonly used polymers in separation process (Albertsson, P. A. et al., "Phase diagrams," *Methods Enzymol.* 1994, 228, 3-13; Dissing, U. et al., "Poly(ethyleneimine) as a phase-forming polymer in aqueous two-phase systems," *Biotechnol. Appl. Biochem.* 1993, 17, 15-21; Bergfeldt, K. et al., "Phase Separation Phenomena and Viscosity Enhancements in Aqueous Mixtures of Poly(styrenesulfonate) with Poly(acrylic acid) at Different Degrees of Neutralization," *Macromolecules.* 1995, 28, 3360-3370; Svensson, M. et al., "Phase Behavior in Aqueous Two-Phase Systems Containing Micelle-Forming Block Copolymers" *Macromolecules.* 1995, 28, 3597-3603—each incorporated herein by reference in its entirety). However, purified dextran is quite expensive and biodegradable (Hughes, P. et al., "Purification of proteins by aqueous two-phase partition in novel acrylic copolymer systems," *Enzyme Microb. Technol.* 1988, 10, 115-122—incorporated herein by reference in its entirety). There have been efforts to develop environment-friendly novel green ATPSs based on ionic liquids (Ba, X.-g. et al., "Application of ionic liquid aqueous two-phase extraction in bioseparation," *Huaxue Shijie.* 2007, 48, 240-242, 251; Li, Z. et al., "Ionic liquid-based aqueous two-phase systems and their applications in green separation processes," *TrAC, Trends Anal. Chem.* 2010, 29, 1336-1346—each incorporated herein by reference in its entirety).

The ATPSs based on hydrophobically modified poly(acrylamide-co-styrene)-POE (Hamad, E. J. et al., "Influence of polymer structure on protein partitioning in two-phase aqueous systems," *Biotechnol. Prog.* 1996, 12, 173-177—incorporated herein by reference in its entirety) and poly[sodium (diallylamino)ethanoate-alt-sulfur dioxide]-POE (Waziri, S. M. et al., "The effect of pH and salt concentration on the coexistence curves of aqueous two-phase systems containing a pH responsive copolymer and polyethylene glycol," *Fluid Phase Equilibria.,* 2003, 205, 275-290; Waziri, S. M. et al., "Protein partitioning in aqueous two-phase systems composed of a pH-responsive copolymer and poly(ethylene glycol)" *Biotechnol. Prog.* 2004, 20, 526-532—each incorporated herein by reference in its entirety) were examined in the study of protein partitioning. Coexistence curves for a variety of ATPSs involving pH-responsive hydrophobically modified ionic cyclocopolymers of poly[sodium (diallylamino)ethanoate-alt-sulfur dioxide] and urethanized poly(ethenol) have been reported (Ali, S. A. "Phase diagrams for urethanized polyvinyl alcohol and a series of hydrophobically modified pH-responsive diallylammonioethanoate cyclopolymers," Korean *J. Chem. Eng.* 2012, 29(10), 1426-1437—incorporated herein by reference in its entirety).

Ionic polymers including polyzwitterions (PZs) and polyampholytes have the potential to be effective components in the construction of ATPSs. The ATPSs involving PZs, which seem to mimic biomolecules like proteins, is expected to impart greater efficiencies in bioseparation involving monomeric amino acids or proteins. With this in mind, the effect of pH and salt concentration on the phase diagram data of new ATPSs involving pH-responsive dianionic polyelectrolytes (DAPE) and POE were examined.

Copolymeric dianionic polyelectrolytes showing pH responsive behavior are now shown to be an effective basis for ATPS. The use of dianionic copolyelectrolytes in combination with a corresponding polymeric material such as a polyoxyalkylene polymer provides an ATPS with beneficial phase separation properties. The ATPSs provide advantages over conventional ATPSs including improved solubility and the ability to undergo regeneration and/or recycling through a precipitation and re-dissolution mechanism.

The charge types and their densities on the polymer chains of the DAPE can be controlled by allowing it to equilibrate with a polyzwitterion (PZ) (e.g., poly[hydrogen (diallylammonio)methylphosphonate-alt-sulfur dioxide]), and a salt (e.g., poly[sodium (diallylammonio)methylphosphonate-alt-sulfur dioxide]), a zwitterionic/anionic polyelectrolyte (ZAPE) under the influence of added HCl. Note that the ZAPE has an interesting blend of zwitterionic and anionic groups in the same repeating unit. The solubility behaviors of the polymers dictate that the DAPE may be used for the construction of recycling ATPS since the pH-responsive polymer can be precipitated at a lower pH value by its conversion to water-insoluble PZ.

BRIEF SUMMARY OF THE INVENTION

In one embodiment the invention includes a cycloalkyl phosphonate sulfonyl polyelectrolyte copolymer.

In another embodiment of the invention the copolymer includes cyclopolymerized units of a diallyl ammonio alkyl phosphonate group.

In another embodiment of the invention the copolymer is in the form of a dianionic polyelectrolyte.

In another embodiment of the invention the copolymer is a dianionic polyelectrolyte of poly[sodium(diallylamino)methylphosphonate-alt-sulfur dioxide].

Another embodiment of the invention includes a composition comprising the copolymeric dianionic polyelectrolyte in combination with a polyoxyalkylene polymer.

Another embodiment of the invention includes an aqueous two-phase system (ATPS) containing a composition comprising the copolymeric dianionic polyelectrolyte and the polyoxyalkylene polymer by treatment with a base and/or acid.

In another embodiment of the invention the ATPS containing the copolymeric dianionic polyelectrolyte and the polyoxyalkylene polymer is used as a matrix for purifying one or more materials.

In another embodiment of the invention the ATPS containing the copolymeric dianionic polyelectrolyte and a polyoxyalkylene polymer is recycled and purified by subjecting the copolymeric dianionic polyelectrolyte to precipitation, purification and isolation.

In another embodiment of the invention the ATPS is recycled by converting the copolymeric dianionic polyelectrolyte to a polyzwitterion by treatment with acid at low pH.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION OF THE INVENTION

The invention includes a copolymeric dianionic polyelectrolyte (DAPE) containing cyclopolymerized units of a diallyl ammonio alkyl phosphonate and sulfur dioxide. The resultant copolymer includes repeating units including a 5-membered heterocyclic ring having a nitrogen atom bonded to units of a sulfonyl group (—$SO_2$—). The sulfonyl group is bonded to the 5-membered heterocyclic ring through an alkylene (e.g., methylene) group and is further bonded to an alkyl phosphonate group. The alkylene group connecting the nitrogen atom of the 5-membered heterocyclic ring and the phosphorous atom of the phosphonate group is, e.g., a $C_1$-$C_6$ alkylene group including, methylene (—$CH_2$—), ethylene (—$C_2H_4$—), propylene (—$C_3H_6$—), butylene (—$C_4H_8$—), pentylene (—$C_5H_{10}$—), or hexylene (—$C_6H_{12}$—) and isomers thereof. The alkylene group connecting the nitrogen atom and the phosphorous atom is preferably a methylene group (—$CH_2$—).

The phosphonate group connected to the nitrogen atom of the 5-membered heterocyclic ring is preferably of formula —P(=O)(OR')$_2$. The R' group of the phosphonate group is preferably an alkyl group selected from the group consisting of methyl, ethyl, propyl, butyl, pentyl or hexyl. Preferably the R' group of the phosphonate is an ethyl group.

The copolymeric dianionic polyelectrolyte includes the following formula (I):

(I)

X is a cationic counterion such as $Na^+$, $K^+$, $Li^+$, $Ca^{2+}$, $Sr^{2+}$, $Sn^{2+}$, $Ba^{2+}$, or $Zn^{2+}$. The n is the number of repeating monomer units of the DAPE. The number of repeating units of the DAPE is in the range of 20-1,500; 40-1,400; 80-1,300; or 100-1,200.

The copolymeric precursor of the dianionic polyelectrolyte is shown in Scheme 1 as CPE 1. Treatment of the copolymeric precursor with acid ($H^+$) under aqueous conditions forms a first product PZ 2 which is a zwitterionic material. Scheme 1 shows the synthesis of the pH—responsive polymer DAPE 4 from cationic polyelectrolyte (CPE) 1. The DAPE polymer can be synthesized by method of Ali, S. et al., "Comparative solution properties of cyclocopolymers having cationic, anionic, zwitterionic and zwitterionic/anionic backbones of similar degree of polymerization." *Polymer.* 2012, 53, 3368-3377, which is incorporated herein by reference in its entirety, with NaCl having a mass fraction of for example >0.995, NaOH having a mass fraction of >0.98, and HCl having a mass fraction of 0.37, with the use of deionized water.

Scheme 1. Synthesis of pH-responsive polymer 4

CPE 1

-continued

The dianionic polyelectrolyte is a copolymer and therefore the copolymeric precursor CPE 1 contains only the monomer units shown in Scheme 1 and no other co-monomer units with the exception that one or more terminating units that are different from the repeating units of the copolymeric backbone may be included. In still a further embodiment of the invention the copolymeric precursor and the copolymeric dianionic polyelectrolyte consist essentially of repeating units of the 5-membered heterocyclic phosphonate sulfonyl repeating and sulfonyl units but include one or more additional monomer units in an amount that is substantially less than the number of repeating units shown in the CPE 1 formula. The microstructure of the polymer includes linear or branched shapes including star polymers, comb polymers, brush polymers and ladder polymers. It is important that the inclusion of any comonomer in a polymer that consists essentially of the 5-membered heterocyclic phosphonate sulfonyl repeating units not materially affect the polyelectrolyte, solubility or pH responsiveness of the copolymeric precursor or the copolymeric dianionic polyelectrolyte derived therefrom.

In Scheme 1 treatment of CPE 1 with an acid, e.g., an inorganic or organic acid such as HCl, $H_2SO_4$, para-toluene sulfonic acid and the like, forms the polyzwitterionic material PZ 2. Treatment of CPE 1 with acid results in ionization and conversion of the OR' groups of the phosphonate to corresponding hydroxy groups. Under acidic conditions at least one of the hydroxy groups of the resultant phosphonate material is anionic and thus balances the cationic charge of the nitrogen atom of the 5-membered heterocyclic ring.

The weight average molecular weight of the copolymeric precursor CPE 1 is in the range of from 6,000-500,000; 12,000-450,000; 24,000-400,000.-g·mol$^{-1}$.

Further treatment of the PZ 2 polyzwitterion with an alkaline material, e.g., NaOH, KOH, Ca(OH)$_2$ and the like, deprotonates the remaining hydroxy group of the phosphonate group to provide a polymeric material having an anionic charge. The anionically charged derivative of the PZ 2 polyelectrolyte is shown as ZAPE 3 (zwitterionic anionic polyelectrolyte) in Scheme 1.

Further treatment with additional base deprotonates the nitrogen atom of the 5-membered heterocyclic ring to form the dianionic polyelectrolyte DAPE 4 shown in Scheme 1. The polydispersity index for DAPE 4 is, for example, in the range of 0.50-3.00, 1.00-2.50, and more preferably 2.00-2.25.

The dianionic polyelectrolyte DAPE can be used as a component of ATPSs, preferably in combination with one or more other polymers such as a polyoxyalkylene. The aqueous two-phase system may comprise water in an amount of 10% by weight, 20% by weight, 30% by weight, 40% by weight, 50% by weight, 60% by weight, 70% by weight, 80% by weight or 90% by weight based on the total weight of the aqueous two-phase system. Either phase of the aqueous two-phase system may comprise water in an amount of 10% by weight, 20% by weight, 30% by weight, 40% by weight, 50% by weight, 60% by weight, 70% by weight, 80% by weight, or 90% by weight based on the weight of a single phase of the two-phase system. The charge type (anionic or cationic) and the amount of charge (charge density) of the copolymeric dianionic polyelectrolyte may be modified by treatment with acid or base. The CPE and the POE may be present in a weight ratio of 0.1:10-10:0.1, preferably 0.5:5-5:0.5, or 1:1.

Polyoxyethylene (POE) can be used as a component of ATPSs in combination with the dianionic polyelectrolyte DAPE. POE forms the hydrophobic upper layer of the system. Polyoxyethylene (H—(O—CH$_2$—CH$_2$)$_n$—OH) may be substituted with other polyoxyalkylenes such as polyoxymethylene (H—(O—CH$_2$)$_n$—OH) and/or polyoxypropylene (H—(O—CH$_2$—CH$_2$—CH$_2$)$_n$OH).

The weight average molecular weight of the polyoxyalkylene polymer is preferably in the range of 10,000-2,000,000, 20,000-1,800,000, 40,000-1,600,000, 80,000-1,500,000, 100,000-1,200,000, 200,000-1,000,000, 300,000-900,000, 400,000-800,000, 500,000-700,000.

The ATPSs may be used to separate proteins and other valuable biological products from reaction systems or extracts by partitioning at least one desirable component into a first phase of the ATPS and one or more less desirable products and/or impurities into a second phase of the ATPSs. The partitioning coefficient of the ATPS may be determined in the manner described in U.S. Pat. No. 7,060,669 (incorporated herein by reference). Partitioning is carried out by mixing a composition comprising desirable biological constituents (proteins) with the ATPS to thereby partition and isolate one or more desirable products in a single phase of the two-phase aqueous system. Representative methods for partitioning biological products include separating one of the phases of the aqueous two-phase system then treating the phase with one or more reagents, e.g., acids or bases, or other agent in order to induce separation of the polyelectrolyte and/or in order to induce separation such as precipitation of the desirable biological product. Partitioning may be carried out by further including one or more detergents or surface active agents in either or both of the phases of the aqueous two-phase system.

The intrinsic viscosity [η] of CPE 1 is determined to be 0.0531 m$^3$·kg$^{-1}$ in solution having NaCl molality ($m_{NaCl}$) of 0.1 mol·kg$^{-1}$ at 303 K. Weight average molar mass ($\overline{M}_w$) of a sample of CPE 1 with an [η] value of 0.0542 m$^3$·kg$^{-1}$ has been reported to be 105 kg·mol$^{-1}$ (PDI: 2.03) determined by the GPC measurement using poly(oxoethylene) as a standard and water as eluent (Ali, S. A. et al., "Comparative solution properties of cyclocopolymers having cationic, anionic, zwitterionic and zwitterionic/anionic backbones of similar degree of polymerization.," *Polymer,* 2012, 53, 3368-3377—incorporated herein by reference in its entirety). Since CPE 1, prepared for the current work, has a similar intrinsic value, its ($\overline{M}_W$) is also expected to be around 100 kg·mol$^{-1}$. The repeating units of CPE 1 and DAPE 4 have molar masses of 0.348 and 0.299 kg·mol$^{-1}$, respectively; thus the $\overline{M}_W$ and $\overline{M}_n$ for the DAPE 4 is calculated to be 86.0 and 42.4 kg·mol$^{-1}$, respectively for a PDI of 2.03. The reduced and intrinsic viscosities of ZAPE 3 and DAPE 4 in the presence of HCl in different salt concentrations are mentioned in Table 2. Poly(oxyethylene) (POE) of number average molar mass ($\overline{M}_n$) of 35.0 kg·mol$^{-1}$ was purchased from MERCK-Schuchardt.

TABLE 2

Viscosity of ZAPE 3$^a$ and DAPE 4$^b$

| Polymer | ($\square$sp/C)$^c$/m$^3$ kg$^{-1}$ | [η]$^d$/m$^3$ kg$^{-1}$ m$_{NaCl}$ of | | |
|---|---|---|---|---|
| | | 0.1 mol·kg$^{-1}$ | 0.25 mol·kg$^{-1}$ | 0.4 mol·kg$^{-1}$ |
| DAPE 4 | 0.0401 | 0.0331 | 0.0291 | 0.0256 |
| DAPE + 0.5 equiv HCl | 0.0259 | — | — | — |
| DAPE + 1 equiv HCl | 0.0120 | — | — | — |
| DAPE + 1.2 equiv HCl | 0.00630 | — | — | — |
| DAPE + 1.4 equiv HCl | Precipitate | — | — | — |
| ZAPE 3 | — | 0.0112 | 0.00989 | 0.00847 |

$^a$poly[sodium(diallylammonio)methylphosphonate-alt-sulfur dixide].
$^b$poly[sodium(diallylamino)methylphosphonate-alt-sulfur dixide].
$^c$Reduced viscosity of a 10 m$^3$ kg$^{-1}$ polymer solution in salt-free and 0.1N NaCl at 30K was measured with a Ubbelohde Viscometer (K = 0.005718).
$^d$Viscosity of 10 to 1.25 m$^3$·kg$^{-1}$ polymer solution in salt-free and m$_{NaCl}$ of 0.1 mol·kg$^{-1}$ at 30 (±0.1)K was measured with a Ubbelohde Viscometer (K = 0.005718).

DAPE 4 is a pH-responsive polyelectrolyte owing to the presence of two negative oxygens and a nitrogen having unquenched valency that permits several equilibrations involving DAPE/ZAPE 5, ZAPE 3, ZAPE/PZ 6, PZ 2, and CPE 7 as shown in Scheme 2. The dominance of a particular form would depend on the pH of the medium. Note that the type of charges and their densities on the polymer backbone can be controlled by addition of NaOH or HCl. In the presence of 0, 0.5, 1, 2, and 3 equivalents of HCl, the dominant form in the equilibrations is expected to be DAPE 4, DAPE/ZAPE 5, ZAPE 3, PZ 2, and CPE 7, respectively as shown in Scheme 2. Note that all the forms are soluble in salt-free water except PZ 2, in which the zwitterionic interactions are so strong that it requires a critical salt concentration (CSC) of 4.73 mol·kg$^{-1}$ NaCl to disrupt the intra- and interchain attractive interactions and permit its water solubility. DAPE 4 upon addition of 1.2 equiv HCl gives water-soluble 6 with a ZAPE/PZ ratio of 80:20, while the form of 6 with a ZAPE/PZ ratio of 60:40, obtained after addition of 1.4 equiv of HCl, becomes water-insoluble as a result of increasing proportion of zwitterionic fraction as presented in Table 2. One of the important advantage of having DAPE as a component in an ATPS is that it can be used as a water-soluble polymer in the form of 3 and 4 above a certain minimum pH, below which it can be recycled by precipitating out in the form of water-insoluble PZ 2.

The solubility behavior (as presented above) and its relationship with the hydrodynamic volume of a polymer chain can be rationalized using equation 4. The screening of the attractive polyampholytic interactions between opposite charges and repulsive Coulombic interactions between similar charges can be described mathematically (Higgs, P. G. et al., "Theory of polyampholyte solutions.," *J. Chem. Phys.* 1991, 94, 1543-54; Candau, F. et al., "Polyampholytes (Properties in Aqueous Solution)," Salamone J C, Ed.; CRC Press: Boca Raton, Fla. 1996, 7, 5462-76; Wittmer, J. et al., "Random and alternating polyampholytes," *Europhys. Lett.* 1993, 24, 263-8; Everaers, R. et al., "Complexation and precipitation in polyampholyte solutions," *Europhys. Lett.* 1997, 37, 275-80; Salamone, J. C. et al., "Aqueous solution properties of a poly(vinyl imidazolium sulphobetaine)," Polymer. 1978, 19, 1157-62—each incorporated herein by reference in its entirety) by the first and second term of equation 4, respectively:

$$v^* = -\frac{\pi(fl_B)^2}{\kappa_s} + \frac{4\pi l_B \Delta f^2}{\kappa_s^2} \quad (4)$$

where v* is the electrostatic excluded volume, $I_B$ is the Bjerrum length, f is the total fraction of charged monomers, Δf is the charge imbalance, and $\kappa_S$ is the Debye-Huckel screening parameter. The solution behavior of ionic polymers with or without charge symmetry is then described by v*: a negative and a positive excluded volume implies contraction and expansion of a polymer chain, respectively. For a electroneutral (±)PZ 2, the solution behavior is described by the screening of the attractive polyampholytic interactions since the second term of eq. 4 becomes zero as a result of Δf=0. The negative v* electrostatic excluded volume indicates contraction to a collapsed polymer chain. The electroneutrality of (±) PZ 2 can not be maintained in the presence of added salt NaCl; it acquires an overall anionic charge since the cationic nitrogens are more effectively screened by Cl$^-$ ions, than the anionic PO$_3^-$ by the Na$^+$. As a result, the presence of NaCl makes v* value a lesser negative thus helping the polymer coil to expand thereby resulting in increased solubility of the polymer.

As the DAPE 4 travels through DAPE/ZAPE 5, ZAPE 3, ZAPE/PZ 6 to electroneutral PZ 2, the charge imbalance Δf decreases progressively. The decreasing importance of the second term in equation 4 with decreasing Δf thus leads to the contraction of polymer coil. This correlates well with the viscosity data shown in Table 2: DAPE 4 has higher viscosity than ZAPE 3 whereas the PZ 2 becomes water-insoluble as a result of its being in a collapsed chain conformation. The viscosity values were found to be decreasing with the increase in NaCl concentration, indicating that as the Δf decreases so as the repulsive contribution by the second term decreases thereby leading to the contraction of the polymer chain. The negative oxygens in DAPE 4 and in the anionic fraction of ZAPE 3 are screened by the Na⁺ ions from the added NaCl and as a result the charge imbalance Δf is minimized.

The following are structural changes in the DAPE polymer in the presence of HCl.

whelmingly rich in POE and DAPE, respectively. The $^1$H NMR spectra of (a) DAPE 4, (b) sample from the bottom phase of system 2 of FIG. 2C and Table 5 (vide infra), and (c) sample from top phase of system 3 of FIG. 2C and Table 5 (vide infra), are displayed in FIG. 1.

Scheme 2. The structural changes in DAPE 4 in the presence of HCl

Scheme 2 describes the effect of acid and base treatment on DAPE 4, the copolymer that results from the treatment of different amounts of acid and/or base includes monomer units having different charge characteristics. For example, reaction of DAPE 4 with 0.5 equivalents of HCl functions to drive one DAPE unit to form a ZAPE unit. The resultant copolymer includes monomer units of different charge characteristics. Further treatment with acid drives the polymer structure to ZAPE 3 which in turn may be treated with a further amount of acid to form a copolymer having differing relative numbers of zwitterionic anionic polyelectrolyte (ZAPE) and polyzwitterion (PZ). Finally, treatment with sufficient amount of acid regenerates the cyclic polyelectrolyte (CPE) which is the copolymeric precursor to DAPE.

Referring now to the drawings, wherein like reference numerals designate identical or corresponding parts throughout the several views.

Figure 1:
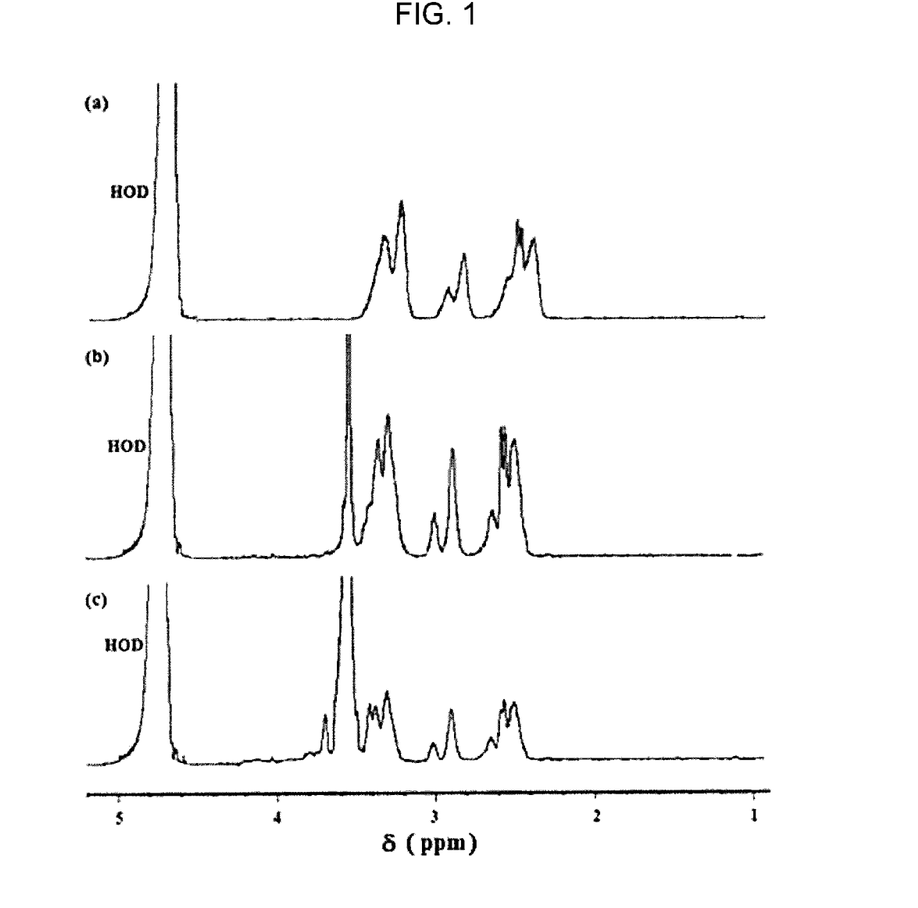
FIG. 1 shows a $^1$H NMR spectra of DAPE 4.
Figure 2A:
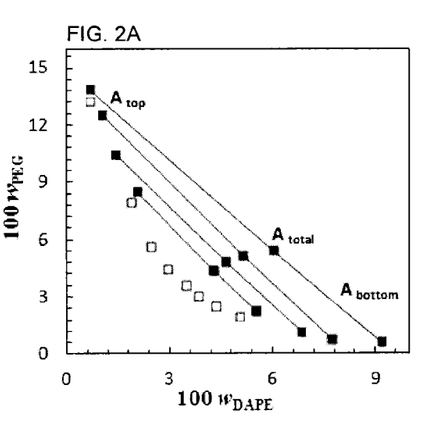
FIGS. 2A-2D show phase diagrams of a composition containing POE+DAPE 4+$H_2O$.
Figure 2B:
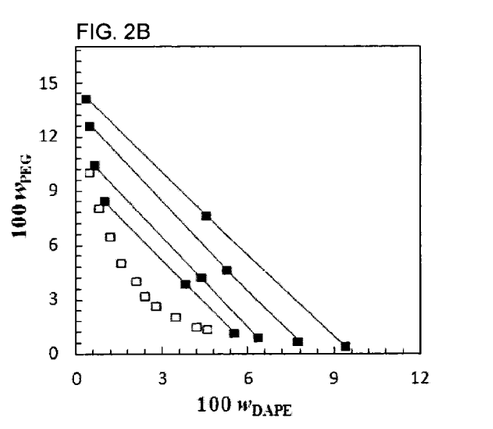
Figure 2C:
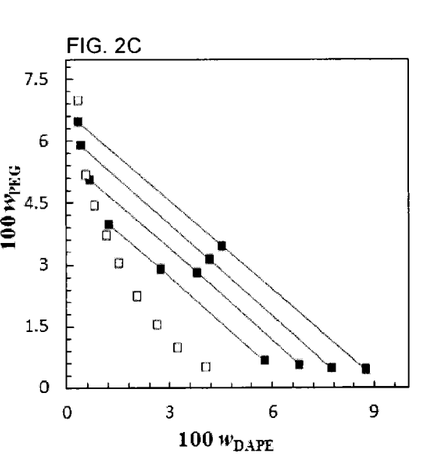

As illustrated in FIG. 1, a $^1$H NMR spectra includes (a) DAPE 4, (b) Bottom phase, system 2, FIG. 2C, Table 5: (DAPE 4, POE, $m_{NaCl}$ of 0.4 mol·kg$^{-1}$, 0.0 equiv. HCl); (c) Top Phase, system 3, FIG. 2C, Table 5: (DAPE 4, POE, $m_{NaCl}$ of 0.4 mol·kg$^{-1}$, 0.0 equiv. HCl).

The stock solutions of DAPE 4 and POE having respective mass fraction (w) of 0.10 to 0.20 and 0.20 were prepared in salt-free water. Several total-systems (≈7 cm$^3$) of known compositions ($A_{total}$) as described in Tables 3-9 were made in calibrated cylinders. The equivalent amount of NaCl, generated in the presence of HCl, is taken into account in the determination of the final salt (NaCl) concentration. The mixtures were shaken thoroughly and centrifuged for a period of 6.0·10$^2$ to 1.2·10$^3$ s to ensure a complete phase separation. After equilibration at 296 K for 24 h, the volume and the density of the top layers (≈1030 kg·m$^{-3}$) and bottom layers (≈1060 kg·m$^{-3}$) were measured. The $^1$H NMR spectra of both layers were measured after exchanging H$_2$O by D$_2$O. FIG. 1 shows that the top and bottom layers were found to be over- The $^1$H NMR signals for the twelve protons of DAPE 4 appeared in the ranges δ2.45 to 3.05 and δ3.10 to 3.60 ppm while the partially overlapping four-proton singlet at δ3.6 were attributed to the POE as shown in FIGS. 1B and 1C. Careful integration of the signals in FIG. 1A in the ranges δ2.25 to 3.05 and δ3.10 to 3.60 ppm revealed their respective areas in a 1.23:1.00 ratio. Note that the signals in the range δ2.45 to 3.05 is free of any overlapping signal and its area (A) is used to calculate the area (B) under δ3.10 to 3.60 attributed to DAPE 4 as A×(1.00/1.23). The area (C) under four-proton overlapping singlet at δ3.6 for the POE was calculated as [D−A×(1.00/1.23)] where D is the total area in the range δ3.10 to 3.60 ppm belonging to the POE as well as a part of DAPE 4. So, the area for a single H for DAPE 4 and POE becomes [A+B]/12 and C/4, respectively. The mole ratio of POE/DAPE 4 (i.e. the ratio of area of single H of POE and DAPE thus becomes:

$$\frac{\text{mol} POE}{\text{mol} DAPE} = \frac{\text{Area of } 1H \text{ of } POE}{\text{Area for } 1H \text{ of } DAPE} = \frac{C/4}{[A+B]/12} \qquad (1)$$

$^1$H NMR measurements permit determination of the mole ratios. The tie lines were constructed using the systems in Tables 2-8. Weight percent of each polymer is determined by using the Equations 2 and 3 as previously described.

$$[DAPE_b] = \frac{POE_o/44.0 - (DAPE_o/\text{MW}_{DAPE})([POE]/[DAPE])_t}{V_b\{([POE]/[DAPE])_b - ([POE][DAPE])_t\}} \qquad (2)$$

where, subscript t and b represent top and bottom phase, respectively. [DAPS] and [POE] represent concentration of the repeating units in mol of repeat unit of DAPE 4 and POE, respectively per kg. $DAPE_0$ and $POE_0$ represent total mass in kg of the respective polymers DAPE 4 and POE, and V represents the volume in m³. For the calculation, molar masses (MW) of the repeat units of the DAPE 4 and POE were taken as 0.299 and 0.440 kg·mol⁻¹, respectively. [POE]/[DAPE] represents molar ratio of the polymers as determined by ¹H NMR integration. The mass of polymer DAPE in the bottom phase is then calculated using:

$$DAPE_b = [DAPE_b]V_b \times 0.299 \quad (3)$$

Once one of the polymer concentrations is known in a phase, then the rest of the concentrations and mass fraction (w) of the polymers in the two phases are calculated from the known volume, density and mass of the two phases.

As illustrated in FIGS. 2 and 3, phase diagrams of DAPE 4-POE-H₂O systems are shown together with data obtained by NMR and turbidity methods. FIGS. 2A-2D illustrate phase diagrams (■ and □ represent data obtained by respective NMR and turbidity method) of [POE+DAPE 4+H₂O] in the presence of: (FIG. 2A) 0.0 equiv. HCl, $m_{NaCl}$ of 0.1 mol·kg⁻¹; (FIG. 2B) 0.0 equiv. HCl, $m_{NaCl}$ of 0.25 mol·kg⁻¹; (FIG. 2C)²⁷ 0.0 equiv. HCl, $m_{NaCl}$ of 0.4 mol·kg⁻¹; (FIG. 2D) The effect of salt concentration on the binodal curve of [POE+DAPE 4+H₂O] system (▲, ■ and ● represent data obtained in $m_{NaCl}$ of 0.1 mol·kg⁻¹, 0.25 mol·kg⁻¹ and 0.4 mol·kg⁻¹, respectively by turbidity method). FIGS. 3A-3E illustrate phase diagrams (■ and Δ represent data obtained by NMR method, and □ represents data from turbidity method) of [POE+DAPE 4+H₂O] in the presence of (FIG. 3A) 0.5 equiv. HCl, $m_{NaCl}$ of 0.25 mol·kg⁻¹; (FIG. 3B) 1.0 equiv. HCl, $m_{NaCl}$ of 0.25 mol·kg⁻¹; (FIG. 3C) 0.5 equiv. HC $m_{NaCl}$ of 0.4 mol·kg⁻¹; (FIG. 3D) 1.0 equiv. HCl, $m_{NaCl}$ of 0.4 mol·kg⁻¹; (FIG. 3E) Effect of HCl and NaCl concentration on the binodal curves of [DAPE 4+POE+H₂O] ATPSs.

In the phase diagrams, the mass fraction (w) of the polymer rich in the top and bottom phase is assigned the y- and x-axis, respectively. The POE and DAPE preferred to stay at the top and bottom phase, respectively. The tie lines in the phase diagrams for each total system of composition $A_{total}$ were constructed by ¹H NMR method which is used to determine the compositions $A_{top}$ and $A_{bottom}$ of the polymers in equilibrium in the top and bottom phases, respectively. The tie lines are helpful in the construction of ATPS with suitable volume ratio of the top and bottom phases as determined by the ratio of the tie line lengths of $A_{total}$-$A_{bot}$ and $A_{total}$-$A_{top}$. The binodal curves were obtained by the turbidity method. The experimental data are shown in Tables 2-8.

Figure 2D:
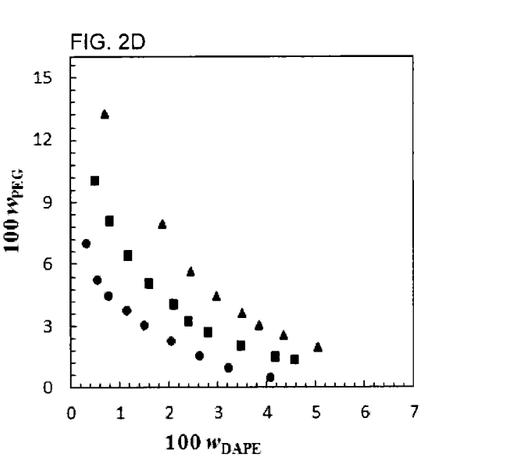
Figure 4A:
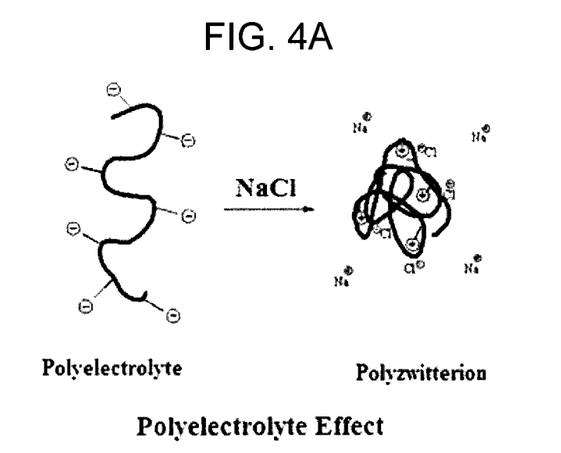
FIGS. 4A-4B show diagrams demonstrating the effect of added salt on the conformation of polyelectrolytes and polyzwitterions.
Figure 4B:
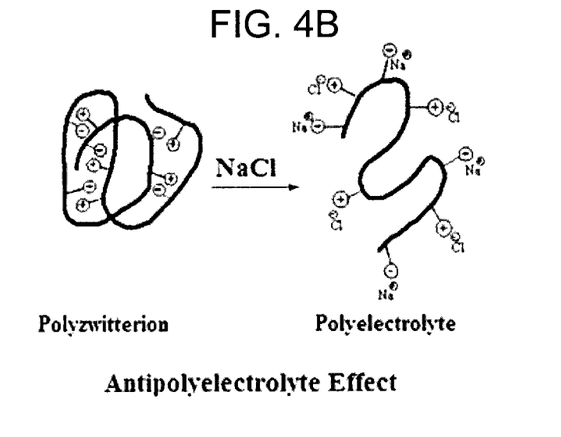
Figure 5A:
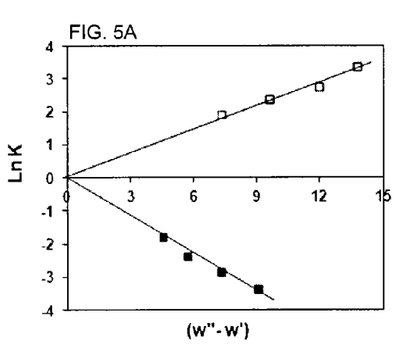
FIGS. 5A-5F show phase diagrams of DAPE 4+POE+HCl systems.
Figure 5B:
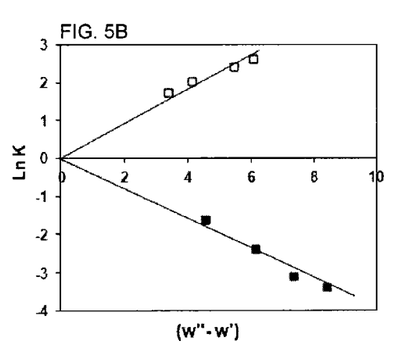
Figure 5C:
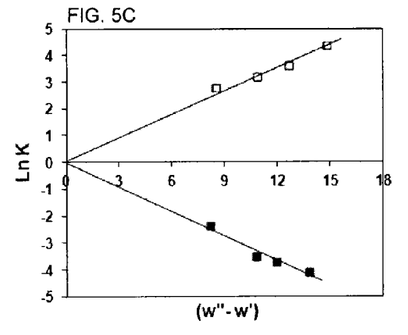
Figure 5D:
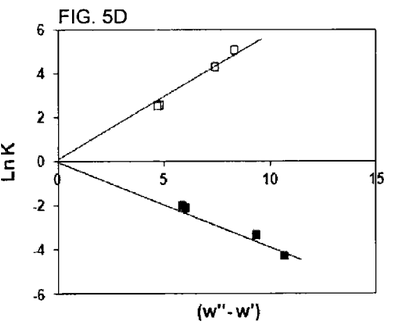
Figure 5E:
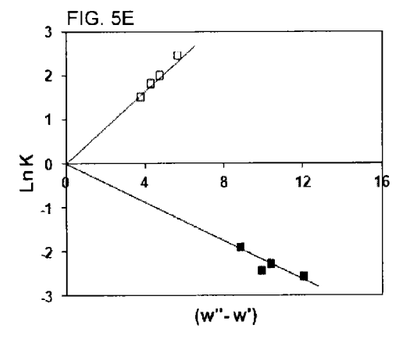
Figure 5F:
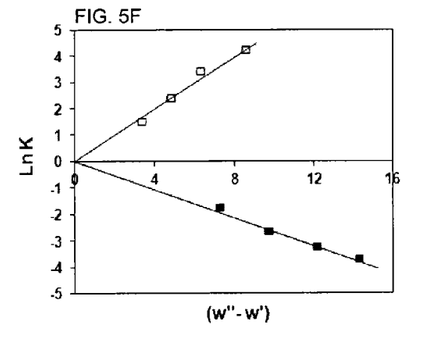

The binodals ascertain the segregative phase separation behavior of the polymers, and their symmetrical shape imply that the two polymers may have very similar hydrodynamic volumes (Ali, S. A. et al.; "Synthesis and aqueous phase behaviour of homo- and co-polymers of 1,1-diallyl-4-formylpiperizinium chloride," *Polymer.* 1997, 38, 3385-3393—incorporated herein by reference in its entirety). The phase formation happening at a total polymer mass fraction of less than 0.10 could be useful from an industrial point of view. The effect of salt concentration on the binodals is shown in FIG. 2D. The binodal curves are shifted downward with the increase in concentration of NaCl. The increase in the salt concentration leads to a decrease in electrostatic repulsion between the poly-electrolyte chains (Dobrynin, A. V., et al., "Adsorption of a Polyampholyte Chain on a Charged Surface," *Macromolecules.* 1997, 30(15), 4332-4341; Van de Steeg, H. G. M. et al., "Polyelectrolyte adsorption: a subtle balance of forces," *Langmuir.* 1992, 8, 2538-2546; Sukhishvili, S. A. et al., "Polyelectrolyte Adsorption onto an Initially-Bare Surface of Opposite Electrical Charge," *J. Chem. Phys.* 1998, 109, 6861-6868; Munk, P. *Introduction to Macromolecular Science*, Wiley/Interscience: New York, 1989—each incorporated herein by reference in its entirety) leading to a compact coiled structure as depicted in FIG. 4. For DAPE 4, addition of salt is thus expected to decrease the hydrodynamic volume of the polymer chain, which in turn makes it less compatible with the POE thereby requiring lesser amounts of polymers for phase separation to occur. Changing the NaCl concentration from 0.1 mol·kg⁻¹ to 0.4 mol·kg⁻¹, leads to a greater contraction of polymer chain of DAPE 4 as evidenced by the reduced [η] given in Table 2. As a result of the greater mismatch of size with the POE, the polymers become the least compatible in $m_{NaCl}$ of 0.4 mol·kg⁻¹.

Figure 3A:
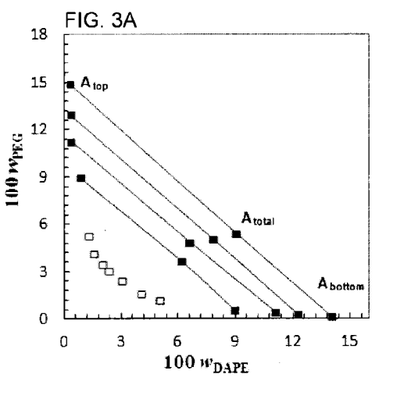
FIGS. 3A-3E show phase diagrams of a composition containing POE+DAPE 4+$H_2O$.
Figure 3B:
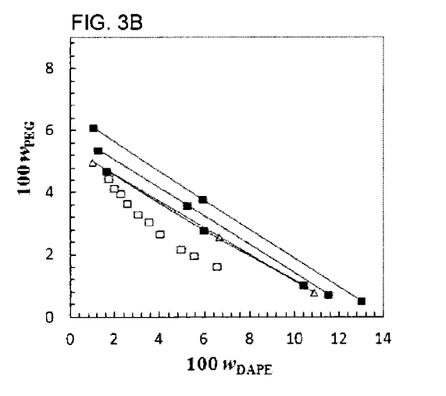
Figure 3C:
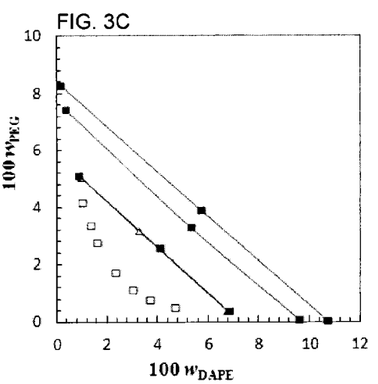
Figure 3D:
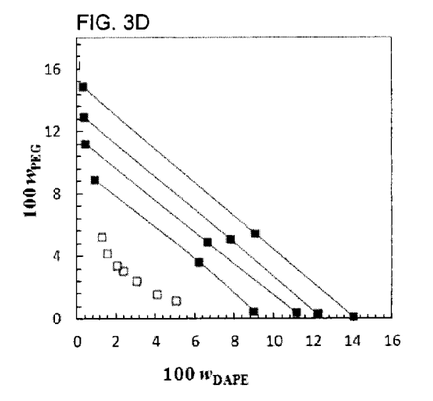
Figure 3E:
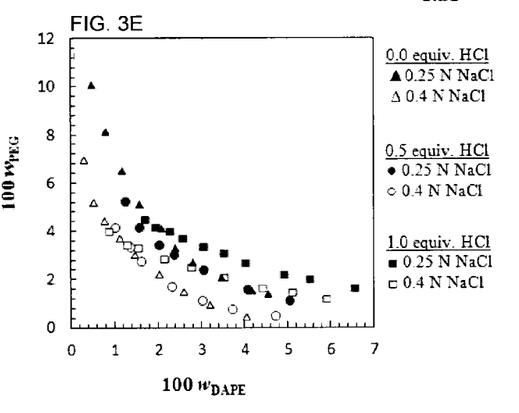

The effects of NaCl concentration and the types of backbone charges (depending on the amount of added HCl) on the binodal curves are displayed in FIG. 3E. The binodal curves are also shifted downward with the increase in concentration of NaCl from 0.25 mol·kg⁻¹ to 0.4 mol·kg⁻¹ in the presence of 0.5 or 1.0 equivalent of HCl. Note that the DAPE 4 (≈100% negative charge) in the presence of 0.5 and 1 equivalent HCl becomes DAPE/ZAPE (=)/(±−) 5 and ZAPE (±−) 3 with a respective charge imbalance (Δf) of 0.60 and 0.33 in favor of the negative charges. The size of the polymer chain decreases with the decrease in □f and leads to greater size-mismatch in the case of ZAPE 3 thereby making it the least compatible with POE. Since all three species (i.e. 3, 4 and 5) have excess negative charges in the polymer backbone, the addition of added salt (NaCl) has thus demonstrated polyelectrolyte effect as revealed in FIG. 4 by decreasing the hydrodynamic volume of the polymers.

The turbidity experiments were carried out at 296 K as described elsewhere (Al-Muallem, H. A., et al., "Synthesis and solution properties of a new ionic polymer and its behavior in aqueous two-phase polymer systems," *Polymer.* 2002, 43(4), 1041-1050—incorporated herein by reference in its entirety). Thus about 1.5 g of a stirred solution of DAPE 4 having mass fraction (w) of ≈0.10 to 0.15 in $m_{NaCl}$ of x mol·kg⁻¹ (x=0, 0.1 or 0.4) was titrated with a known mass of a concentrated solution (w: 0.20) of the POE in $m_{NaCl}$ of x mol·kg⁻¹ until the transparent system turned turbid. Then a known weight of a NaCl solution x mol·kg⁻¹ was added until the system became transparent again. At this point, the composition of the two polymers corresponds to a point on the binodal curve. The process was repeated to obtain more points using more POE to make the mixture turbid followed by addition of NaCl solution of x mol·kg⁻¹ to make it transparent. In order to obtain points on the other end of the binodal, the concentrated solution of the POE was titrated with the DAPE 4 solution using same way as described above.

As illustrated in FIGS. 2A-2D, phase diagrams are shown of representative data of [POE+DAPE 4+H₂O], where ■ and □ represent data obtained by respective NMR and turbidity method.

FIG. 2A represents a phase diagram of [POE+DAPE 4+H₂O] in the presence of 0.0 equiv. HCl, $m_{NaCl}$ of 0.1 mol·kg⁻¹. Table 3, as illustrated below, demonstrates the phase composition of the phase composition of the [POE$^a$±DAPE 4$^b$] System at 296 K.

TABLE 3

Phase Composition of the [POE[a] + DAPE 4[b]] System at 296K (0.0 equiv. HCl, $m_{NaCl}$ of 0.1 mol · kg$^{-1}$) shown in FIG. 2A

| | NMR method | | | | | | |
|---|---|---|---|---|---|---|---|
| | Total system | | Top phase | | Bottom phase | | |
| System | POE w × 100 | DAPE w × 100 | POE w × 100 | DAPE w × 100 | POE w × 100 | DAPE w × 100 | Volume ratio[c] |
| 1 | 5.46 | 5.98 | 13.89 | 0.65 | 0.65 | 9.15 | 0.65 |
| 2 | 5.19 | 5.12 | 12.53 | 1.02 | 0.79 | 7.71 | 0.88 |
| 3 | 4.90 | 4.60 | 10.50 | 1.40 | 1.20 | 6.80 | 0.95 |
| 4 | 4.41 | 4.25 | 8.53 | 2.04 | 2.26 | 5.48 | 0.57 |

| | Turbidity method | | | | |
|---|---|---|---|---|---|
| | Binodal data | | | Binodal data | |
| System | POE w × 100 | DAPE w × 100 | System | POE w × 100 | APE w × 100 |
| a | 13.29 | 0.65 | e | 3.70 | 3.44 |
| b | 8.05 | 1.83 | f | 3.10 | 3.80 |
| c | 5.70 | 2.40 | g | 2.60 | 4.30 |
| d | 4.50 | 2.92 | h | 2.01 | 5.01 |

[a]poly(oxyethylene) of molar mass 35.0 kg mol$^{-1}$.
[b]poly[sodium(diallylamino)methylphosphonate-alt-sulfur dixide].
[c]Volume ratio of top and bottom phase.

FIG. 2B represents a phase diagram of [POE+DAPE 4+H$_2$O] in the presence of 0.0 equiv. HCl, $m_{NaCl}$ of 0.25 mol·kg$^{-1}$. Table 4, as illustrated below, demonstrates the phase composition of the [POE[a]+DAPE 4[b]] system at 296 K.

FIG. 2C represents a phase diagram of [POE+DAPE 4+H$_2$O] in the presence of 0.0 equiv. HCl, $m_{NaCl}$ of 0.4 mol·kg$^{-1}$. Table 5, as illustrated below, demonstrates the phase composition of the [POE[a]+DAPE 4[b]] system at 296 K.

TABLE 4

Phase Composition of the [POE[a] + DAPE 4[b]] System at 296K (0.0 equiv. HCl, $m_{NaCl}$ of 0.25 mol · kg$^{-1}$) shown in FIG. 2B

| | NMR method | | | | | | |
|---|---|---|---|---|---|---|---|
| | Total system | | Top phase | | Bottom phase | | |
| System | POE w × 100 | DAPE w × 100 | POE w × 100 | DAPE w × 100 | POE w × 100 | DAPE w × 100 | Volume ratio[c] |
| 1 | 7.72 | 4.51 | 14.2 | 0.33 | 0.47 | 9.37 | 1.17 |
| 2 | 4.71 | 5.21 | 12.7 | 0.45 | 0.79 | 7.71 | 0.51 |
| 3 | 4.32 | 4.31 | 10.5 | 0.61 | 0.97 | 6.32 | 0.54 |
| 4 | 3.98 | 3.75 | 8.52 | 0.96 | 1.23 | 5.48 | 0.6 |

| | Turbidity method | | | | |
|---|---|---|---|---|---|
| | Binodal data | | | Binodal data | |
| System | POE w × 100 | DAPE w × 100 | System | POE w × 100 | APE w × 100 |
| a | 10.1 | 0.464 | f | 3.31 | 2.37 |
| b | 8.14 | 0.765 | g | 2.73 | 2.77 |
| c | 6.52 | 1.15 | h | 2.11 | 3.45 |
| d | 5.13 | 1.56 | i | 1.56 | 4.15 |
| e | 4.11 | 2.06 | j | 1.41 | 4.53 |

[a]poly(oxyethylene) of molar mass 35.0 kg mol$^{-1}$.
[b]poly[sodium(diallylamino)methylphosphonate-alt-sulfur dixide].
[c]Volume ratio of top and bottom phase.

TABLE 5

Phase Composition of the [POE[a] + DAPE 4[b]] System at 296K (0.0 equiv. HCl, $m_{NaCl}$ of 0.4 mol · kg$^{-1}$) shown in FIG. 2C NMR method

| System | Total system POE w × 100 | Total system DAPE w × 100 | Top phase POE w × 100 | Top phase DAPE w × 100 | Bottom phase POE w × 100 | Bottom phase DAPE w × 100 | Volume ratio[c] |
|---|---|---|---|---|---|---|---|
| 1 | 3.50 | 4.50 | 6.50 | 0.30 | 0.45 | 8.70 | 0.97 |
| 2 | 3.18 | 4.10 | 5.94 | 0.36 | 0.51 | 7.68 | 0.98 |
| 3 | 2.85 | 3.77 | 5.10 | 0.63 | 0.59 | 6.75 | 0.99 |
| 4 | 2.95 | 2.69 | 4.03 | 1.18 | 0.69 | 5.71 | 2.06 |

Turbidity method

| System | Binodal data POE w × 100 | Binodal data DAPE w × 100 | System | Binodal data POE w × 100 | Binodal data APE w × 100 |
|---|---|---|---|---|---|
| a | 7.02 | 0.29 | f | 2.26 | 2.01 |
| b | 5.25 | 0.50 | g | 1.57 | 2.58 |
| c | 4.50 | 0.74 | h | 0.99 | 3.19 |
| d | 3.77 | 1.11 | I | 4.00 | 0.51 |
| e | 3.08 | 1.45 | | | |

[a]poly(oxyethylene) of molar mass 35.0 kg mol$^{-1}$.
[b]poly[sodium(diallylamino)methylphosphonate-alt-sulfur dixide].
[c]Volume ratio of top and bottom phase.

FIG. 2D represents the effect of salt concentration on the binodal curve of [POE+DAPE 4+H$_2$O] system (▲, ■ and ● represent data obtained in $m_{NaCl}$ of 0.1 mol·kg$^{-1}$, 0.25 mol·kg$^1$ and 0.4 mol·kg$^{-1}$, respectively by turbidity method). The binodal curves are shifted downward with the increase in concentration of NaCl. The increase in the salt concentration leads to a decrease in electrostatic repulsion between the poly-electrolyte chains leading to a compact coiled structure as depicted in FIG. 4.

As illustrated in FIGS. 3A-3E, phase diagrams are shown of representative data of [POE+DAPE 4+H$_2$O], where (■ and Δ represent data obtained by NMR method, and □ represents data from turbidity method).

FIG. 3A represents a phase diagram of [POE+DAPE 4+H$_2$O] in the presence of 0.5 equiv. HCl, $m_{NaCl}$ of 0.25 mol·kg$^{-1}$. Table 6, as illustrated below, demonstrates the phase composition of the [POE[a]+DAPE 4[b]] system at 296 K.

TABLE 6

Phase Composition of the [POE[a] + DAPE 4[b]] System at 296K (0.5 equiv. HCl, $m_{NaCl}$ of 0.25 mol · kg$^{-1}$) shown in FIG. 3A NMR method

| System | Total system POE w × 100 | Total system DAPE w × 100 | Top phase POE w × 100 | Top phase DAPE w × 100 | Bottom phase POE w × 100 | Bottom phase DAPE w × 100 | Volume ratio[c] |
|---|---|---|---|---|---|---|---|
| 1 | 5.47 | 9.00 | 14.97 | 0.23 | 0.19 | 14.00 | 0.58 |
| 2 | 5.10 | 7.80 | 13.00 | 0.30 | 0.34 | 12.22 | 0.57 |
| 3 | 4.89 | 6.60 | 11.3 | 0.34 | 0.45 | 11.1 | 0.71 |
| 4 | 3.68 | 6.15 | 9.00 | 0.82 | 0.55 | 8.93 | 0.53 |

Turbidity method

| System | Binodal data POE w × 100 | Binodal data DAPE w × 100 | System | Binodal data POE w × 100 | Binodal data APE w × 100 |
|---|---|---|---|---|---|
| a | 1.20 | 5.03 | f | 4.23 | 1.55 |
| b | 1.65 | 4.06 | g | 5.30 | 1.23 |
| c | 2.47 | 3.02 | | | |
| d | 3.08 | 2.36 | | | |
| e | 3.48 | 2.01 | | | |

[a]poly(oxyethylene) of molar mass 35.0 kg mol$^{-1}$.
[b]poly[sodium(diallylamino)methylphosphonate-alt-sulfur dixide].
[c]Volume ratio of top and bottom phase.

FIG. 3B represents a phase diagram of [POE+DAPE 4+H$_2$O] in the presence of 1.0 equiv. HCl, m$_{NaCl}$ of 0.25 mol·kg$^{-1}$. Table 7, as illustrated below, demonstrates the phase composition of the [POE$^a$+DAPE 4$^b$] system at 296 K.

FIG. 3D represents a phase diagram of [POE+DAPE 4+H$_2$O] in the presence of 1.0 equiv. HCl, m$_{NaCl}$ of 0.4 mol·kg$^{-1}$. Table 9, as illustrated below, demonstrates the phase composition of the [POE$^a$+DAPE 4$^b$] system at 296 K.

TABLE 7

Phase Composition of the [POE$^a$ + DAPE 4$^b$] System at 296K (1.0 equiv. HCl, m$_{NaCl}$ of 0.25 mol · kg$^{-1}$) shown in FIG. 3B NMR method

| System | Total system POE w × 100 | Total system DAPE w × 100 | Top phase POE w × 100 | Top phase DAPE w × 100 | Bottom phase POE w × 100 | Bottom phase DAPE w × 100 | Volume ratio$^c$ |
|---|---|---|---|---|---|---|---|
| 1 | 3.80 | 5.90 | 6.12 | 1.02 | 0.53 | 13.00 | 1.48 |
| 2 | 3.60 | 5.20 | 5.40 | 1.20 | 0.73 | 11.50 | 1.60 |
| 3 | 2.61 | 6.62 | 5.02 | 0.98 | 0.81 | 10.86 | 0.74 |
| 4 | 2.80 | 5.93 | 4.74 | 1.58 | 1.05 | 10.37 | 1.00 |

Turbidity method

| System | Binodal data POE w × 100 | Binodal data DAPE w × 100 | System | Binodal data POE w × 100 | Binodal data APE w × 100 |
|---|---|---|---|---|---|
| a | 1.67 | 6.54 | f | 3.35 | 3.02 |
| b | 2.03 | 5.50 | g | 3.71 | 2.55 |
| c | 2.21 | 4.90 | h | 4.00 | 2.24 |
| d | 2.70 | 4.00 | I | 4.20 | 1.94 |
| e | 3.10 | 3.50 | J | 4.50 | 1.69 |

$^a$poly(oxyethylene) of molar mass 35.0 kg mol$^{-1}$.
$^b$poly[sodium(diallylamino)methylphosphonate-alt-sulfur dixide].
$^c$Volume ratio of top and bottom phase.

FIG. 3C represents a phase diagram of [POE+DAPE 4+H$_2$O] in the presence of 0.5 equiv. HCl, m$_{NaCl}$ of 0.4 mol·kg$^{-1}$. Table 8, as illustrated below, demonstrates the phase composition of the [POE$^a$+DAPE 4$^b$] system at 296 K.

TABLE 8

Phase Composition of the [POE$^a$ + DAPE 4$^b$] System at 296K (0.5 equiv. HCl, m$_{NaCl}$ of 0.4 mol · kg$^{-1}$) shown in FIG. 3C NMR method

| System | Total system POE w × 100 | Total system DAPE w × 100 | Top phase POE w × 100 | Top phase DAPE w × 100 | Bottom phase POE w × 100 | Bottom phase DAPE w × 100 | Volume ratio$^c$ |
|---|---|---|---|---|---|---|---|
| 1 | 3.90 | 5.70 | 8.30 | 0.15 | 0.05 | 10.7 | 0.91 |
| 2 | 3.295 | 5.31 | 7.45 | 0.36 | 0.10 | 9.57 | 0.85 |
| 3 | 2.57 | 4.06 | 5.14 | 0.85 | 0.40 | 6.78 | 0.86 |
| 4 | 3.17 | 3.26 | 5.04 | 0.96 | 0.40 | 6.74 | 1.50 |

Turbidity method

| System | Binodal data POE w × 100 | Binodal data DAPE w × 100 | System | Binodal data POE w × 100 | Binodal data APE w × 100 |
|---|---|---|---|---|---|
| a | 0.53 | 4.70 | e | 2.80 | 1.60 |
| b | 0.80 | 3.70 | f | 3.40 | 1.35 |
| c | 1.15 | 3.01 | g | 4.20 | 1.01 |
| d | 1.77 | 2.30 | | | |

$^a$poly(oxyethylene) of molar mass 35.0 kg mol$^{-1}$.
$^b$poly[sodium(diallylamino)methylphosphonate-alt-sulfur dixide].
$^c$Volume ratio of top and bottom phase.

TABLE 9

Phase Composition of the [POE$^a$ + DAPE 4$^b$] System at 296K (1 equiv. HCl, $m_{NaCl}$ of 0.4 mol · kg$^{-1}$) shown in FIG. 3D NMR method

| System | Total system POE w × 100 | Total system DAPE w × 100 | Top phase POE w × 100 | Top phase DAPE w × 100 | Bottom phase POE w × 100 | Bottom phase DAPE w × 100 | Volume ratio$^c$ |
|---|---|---|---|---|---|---|---|
| 1 | 4.24 | 7.42 | 8.64 | 0.36 | 0.12 | 14.58 | 1.00 |
| 2 | 3.67 | 5.93 | 6.49 | 0.497 | 0.20 | 12.58 | 1.17 |
| 3 | 2.90 | 5.50 | 5.20 | 0.76 | 0.47 | 10.4 | 1.02 |
| 4 | 2.63 | 4.74 | 4.20 | 1.57 | 0.88 | 8.78 | 1.24 |

Turbidity method

| System | Binodal data POE w × 100 | Binodal data DAPE w × 100 | System | Binodal data POE w × 100 | Binodal data APE w × 100 |
|---|---|---|---|---|---|
| a | 1.20 | 5.90 | f | 2.88 | 2.13 |
| b | 1.45 | 5.10 | g | 3.33 | 1.53 |
| c | 1.67 | 4.40 | h | 3.47 | 1.29 |
| d | 2.11 | 3.50 | I | 4.00 | 0.87 |
| e | 2.50 | 2.76 | | | |

$^a$poly(oxyethylene) of molar mass 35.0 kg mol$^{-1}$.
bpoly[sodium(diallylamino)methylphosphonate-alt-sulfur dixide].
$^c$Volume ratio of top and bottom phase.

The effects of NaCl concentration and the types of backbone charges (depending on the amount of added HCl) on the binodal curves are displayed in FIG. 3E. The binodal curves are shifted downward with the increase in concentration of NaCl from 0.25 mol·kg$^{-1}$ to 0.4 mol·kg$^{-1}$ in the presence of 0.5 or 1.0 equivalent of HCl.

As illustrated in FIG. 4, the effect of added salt on the conformation of polyelectrolytes and polyzwitterions is shown. As the DAPE 4 travels through DAPE/ZAPE 5, ZAPE 3, ZAPE/PZ 6 to electroneutral PZ 2, the charge imbalance Δf decreases progressively. The decreasing importance of the second term in equation 4 with decreasing Δf thus leads to the contraction of polymer coil. This correlates well with the viscosity data shown in Table 2: DAPE 4 has higher viscosity than ZAPE 3 whereas the PZ 2 becomes water-insoluble as a result of its being in a collapsed chain conformation. The viscosity values were found to be decreasing with the increase in NaCl concentration, indicating that as the Δf decreases so as the repulsive contribution by the second term decreases thereby leading to the contraction of the polymer chain. The negative oxygens in DAPE 4 and in the anionic fraction of ZAPE 3 are screened by the Na$^+$ ions from the added NaCl and as a result the charge imbalance Δf is minimized.

As depicted in FIG. 4, for DAPE 4, addition of salt is thus expected to decrease the hydrodynamic volume of the polymer chain, which in turn makes it less compatible with the POE thereby requiring lesser amounts of polymers for phase separation to occur. Changing the NaCl concentration from 0.1 mol·kg$^{-1}$ to 0.4 mol·kg$^{-1}$, leads to a greater contraction of polymer chain of DAPE 4 as evidenced by the reduced [□] given in Table 2. As a result of the greater mismatch of size with the POE, the polymers become the least compatible in $m_{NaCl}$ of 0.4 mol·kg$^1$.

As illustrated in FIGS. 5A-5F, the phase systems of DAPE 4+POE+HCl using the method of Diamond and Hsu: using the tie line data of: (a) FIG. 2B; (b) FIG. 2C; (c) FIG. 3A; (d) FIG. 3C; (e) FIG. 3B; (f) FIG. 3D are shown. The consistency of the tie-lines of the [DAPE 4-POE-H$_2$O (NaCl)] systems was checked using the following correlation developed by Diamond & Hsu (Diamond, A. D. et al., "Correlation of polymer partitioning in aqueous two-phase systems," AIChE Symp. Ser. 1992, 290, 105-111; Diamond, A. D. Doctoral thesis, "Fundamental Studies of Biomolecule Partitioning in Aqueous Polymer Two-Phase Systems," Lehigh University, Pennsylvania—each incorporated herein by reference in its entirety) based on Flory-Huggins theory:

$$LnK_1 = A_1(w_1'' - w_1') \qquad (5)$$

and $$LnK_2 = A_2(w_2'' - w_2') \qquad (6)$$

where w" and w' are the polymer mass percent (i.e. w×100) in the top and bottom phase, respectively, the slopes $A_1$ and $A_2$ are functions of the polymer molar mass and the interactions between the polymers and water, $K_1$ and $K_2$ represent the partition coefficient ($C_t/C_b$) of the polymer between the top and bottom phase, and the subscripts 1 and 2 represent polymer 1 (DAPE 4) and polymer 2 (POE). Straight line plots for the correlation results ascertain the satisfactory representation of the phase behaviour by this model as shown in FIG. 5. FIGS. 5A-5F illustrate the correlation of the phase diagrams of DAPE 4+POE+HCl systems using the method of Diamond and Hsu: using the tie line data of: (FIG. 5A) FIG. 2B; (FIG. 5B) FIG. 2C; (FIG. 5C) FIG. 3A; (FIG. 5D) FIG. 3C; (FIG. 5E) FIG. 3B; (FIG. 5F) FIG. 3D.

The adjustable parameter A of the partition constant correlation was obtained by using a linear regression between the experimental and the calculated partition constants obtained from equations 5 and 6; values of the root mean-square deviation (rmsd) and the adjustable parameter are presented in Table 10, rmsd value were obtained by equation 7 (Shahriari, S. et al., "Partitioning of cephalexin in aqueous two-phase systems containing poly(ethylene glycol) and sodium citrate salt at different temperatures," J. Chem. Eng. Data 2012, 57, 256-262—incorporated herein by reference in its entirety):

$$rmsd = \frac{\sqrt{\sum_{i=1}^{N}(K_{exp}-K_{calc})_i^2}}{N} \quad (7)$$

where N is the number of tie lines. The experimental data of the partition coefficients were correlated with the equations proposed by diamond and Hsu; the results in Table 10 show that that Diamond and Hsu equations based on Flory-Huggins model can accurately correlate with the data collected in this work.

TABLE 10

Values for constant parameter A introduced in equation 5 and equation 6 along with the rmsd of the model from the experimental data of the partition coefficients

| | DAPE 4[a] | | POE[b] | |
|---|---|---|---|---|
| System | $A_1$ | rmsd | $A_2$ | rmsd |
| POE + DAPE 4 + 0 equiv HCl + $m_{NaCl}$ of 0.25 mol · kg$^{-1}$ | −0.303 | 0.00593 | 0.231 | 0.231 |
| POE + DAPE 4 + 0 equiv HCl + $m_{NaCl}$ of 0.4 mol · kg$^{-1}$ | −0.397 | 0.0106 | 0.466 | 0.748 |
| POE + DAPE 4 + 0.5 equiv HCl + $m_{NaCl}$ of 0.25 mol · kg$^{-1}$ | −0.307 | 0.00276 | 0.298 | 1.83 |
| POE + DAPE 4 + 0.5 equiv HCl + $m_{NaCl}$ of 0.4 mol · kg$^{-1}$ | −0.373 | 0.00806 | 0.588 | 9.50 |
| POE + DAPE 4 + 1.0 equiv HCl + $m_{NaCl}$ of 0.25 mol · kg$^{-1}$ | −0.222 | 0.00633 | 0.430 | 0.158 |
| POE + DAPE 4 + 1.0 equiv HCl + $m_{NaCl}$ of 0.4 mol · kg$^{-1}$ | −0.262 | 0.00719 | 0.513 | 2.55 |

[a]poly[sodium(diallylamino)methylphosphonate-alt-sulfur dioxide].
[b]poly(oxyethylene) of molar mass 35.0 kg mol$^{-1}$.

A pH-responsive polyaminophosphonate DAPE 4 was used in the construction of aqueous two-phase systems with POE. The effect of pH and salt on the binodal curves was investigated. The two polymers were found to form ATPS at low concentrations, where the addition of HCl changed the charge types and their densities on the polymer chains. The increasing concentration of NaCl shifted the binodals downward thereby requiring lesser concentration of the polymers to form ATPS. One of the most gratifying aspects of DAPE 4 is its almost zero solubility in water in the presence of HCl which transforms the polymer to PZ 2. The solubility behavior thus makes it a suitable component for the construction of recycling ATPSs where the polymer can be effectively removed and recycled. The aminophosphonate residues in 4 and 3 mimic biomolecules like proteins, and as such the ATPSs may be used in bioseparation involving monomeric amino acids or proteins. Variable charge densities in the polymer backbone may be exploited in selecting and separating certain proteins in the newly developed ATPSs.

The invention claimed is:

1. A copolymeric dianionic polyelectrolyte having the following formula (I):

(I)

where X is a cationic counter ion selected from the group consisting of Na$^+$, K$^+$ and Li$^+$; and
where n is an integer of 10 or greater.

2. The polyelectrolyte of claim 1, where n is greater than 20.

3. The polyelectrolyte of claim 1, the weight average molecular weight of the DAPE is from 10,000-2,000,000 g·mol$^{-1}$.

4. A composition comprising the copolymeric dianionic polyelectrolyte of claim 1 and one or more polyoxyalkylene polymers.

5. The composition of claim 4 further comprising water.

6. An aqueous two-phase system comprising the copolymeric dianionic polyelectrolyte of claim 1 and a polyoxyalkylene polymer,
wherein the dianionic polyelectrolyte copolymer is present in a first phase of the two-phase system in an amount of at least 70% by weight based on the total weight of the dianionic polyelectrolyte in the aqueous two-phase system; and
wherein the polyoxyalkylene polymer is present in a second phase of the two-phase system in an amount of at least 70% by weight based on the total weight of the polyoxyalkylene polymer in the aqueous two-phase system.

7. A method for regenerating or recycling the dianionic polyelectrolyte copolymer of claim 1, comprising:
mixing an acid with a composition comprising the dianionic polyelectrolyte in an amount sufficient to form a polyzwitterion of the following formula:

where n is an integer of 10 or greater; and
precipitating and isolating the polyzwitterion from the composition; and
reacting the polyzwitterion separated from the composition with a base to form the copolymeric dianionic polyelectrolyte.

8. A method for isolating a protein, comprising:
mixing a composition comprising the protein with the aqueous two-phase system of claim 6;
concentrating the protein in one phase of the aqueous two-phase system and separating the phase containing the protein from the aqueous two-phase system;
isolating the protein from the phase separated from the aqueous two-phase system.

* * * * *

UNITED STATES PATENT AND TRADEMARK OFFICE
CERTIFICATE OF CORRECTION

PATENT NO. : 8,906,972 B1
APPLICATION NO. : 14/142191
DATED : December 9, 2014
INVENTOR(S) : Othman C. S. Al-Hamouz et al.

It is certified that error appears in the above-identified patent and that said Letters Patent is hereby corrected as shown below:

ON THE TITLE PAGE, ITEM (54) AND IN THE SPECIFICATION, COLUMN 1, should read:

AQUEOUS TWO PHASE SYSTEMS (ATPSs) OF pH-RESPONSIVE POLY(PHOSPHONATE-ALT-SULFUR DIOXIDE) WITH PEG

ON THE TITLE PAGE (71) Applicants should read: King Fahd University of Petroleum and Minerals, Dhahran (SA); King Abdulaziz City for Science and Technology, Riyadh (SA)

(73) Assignees should read: King Fahd University of Petroleum and Minerals, Dhahran (SA); King Abdulaziz City for Science and Technology, Riyadh (SA)

Signed and Sealed this
Twentieth Day of October, 2015

Michelle K. Lee
*Director of the United States Patent and Trademark Office*